United States Patent
Brooks et al.

(10) Patent No.: US 11,617,594 B2
(45) Date of Patent: Apr. 4, 2023

(54) SENSOR FILM FOR ENDOSCOPIC INSTRUMENTS

(71) Applicant: Forcen Inc., Toronto (CA)

(72) Inventors: Robert Brooks, Toronto (CA); Justin Wee, Toronto (CA); Justin Gerstle, Toronto (CA); Thomas Looi, Markham (CA); James Drake, Toronto (CA)

(73) Assignee: Forcen Inc., Toronto (CA)

( * ) Notice: Subject to any disclaimer, the term of this patent is extended or adjusted under 35 U.S.C. 154(b) by 629 days.

(21) Appl. No.: 16/072,834

(22) PCT Filed: Jan. 27, 2017

(86) PCT No.: PCT/CA2017/050103
§ 371 (c)(1),
(2) Date: Jul. 25, 2018

(87) PCT Pub. No.: WO2017/127944
PCT Pub. Date: Aug. 3, 2017

(65) Prior Publication Data
US 2019/0059921 A1    Feb. 28, 2019

Related U.S. Application Data

(60) Provisional application No. 62/289,120, filed on Jan. 29, 2016.

(51) Int. Cl.
*A61B 17/29* (2006.01)
*A61B 5/06* (2006.01)
(Continued)

(52) U.S. Cl.
CPC .............. *A61B 17/29* (2013.01); *A61B 5/067* (2013.01); *A61B 5/6847* (2013.01);
(Continued)

(58) Field of Classification Search
CPC .............. A61B 17/29; A61B 2562/164; A61B 2562/0261; A61B 2562/22;
(Continued)

(56) References Cited

U.S. PATENT DOCUMENTS

| | | | | |
|---|---|---|---|---|
| 5,902,248 A | * | 5/1999 | Millar | A61B 8/12 600/485 |
| 2007/0078459 A1 | * | 4/2007 | Johnson | A61B 17/320016 606/51 |
| 2011/0046637 A1 | * | 2/2011 | Patel | A61B 17/29 606/130 |

* cited by examiner

Primary Examiner — Anh T Dang
(74) Attorney, Agent, or Firm — Aird & McBurney LP

(57) ABSTRACT

An endoscopic instrument for use with a trocar, said endoscopic instrument comprising an elongate shaft body having a proximal end and a distal end; an end effector assembly at said distal end operable by manipulation of actuator mechanism at said proximal end; a substrate core having a first surface and a second surface; at least one sensing element on said first surface, said at least one sensing element located adjacent to said distal end; an electronics module for receiving sensed signals from said at least one sensing element, said electronics module located adjacent to said proximal end; a first conductive layer residing on said first surface, said first conductive layer having first solder mask coated thereon; a second conductive layer residing on said second surface, second conductive layer having a second solder mask coated thereon, and wherein said second conductive layer coupled to said at least one sensing element relays said sensed signals from said at least one sensing element to said electronics module and said a first conductive layer is grounded.

18 Claims, 6 Drawing Sheets

(51) Int. Cl.
  *A61B 90/00* (2016.01)
  *A61B 17/28* (2006.01)
  *A61B 5/00* (2006.01)
  *A61B 17/00* (2006.01)
(52) U.S. Cl.
  CPC ............... *A61B 2017/0011* (2013.01); *A61B 2017/00026* (2013.01); *A61B 2017/00044* (2013.01); *A61B 2017/00057* (2013.01); *A61B 2017/00084* (2013.01); *A61B 2017/00115* (2013.01); *A61B 2017/00221* (2013.01); *A61B 2017/00734* (2013.01); *A61B 2017/2825* (2013.01); *A61B 2017/2901* (2013.01); *A61B 2017/2902* (2013.01); *A61B 2017/2905* (2013.01); *A61B 2017/2908* (2013.01); *A61B 2017/2926* (2013.01); *A61B 2090/064* (2016.02); *A61B 2090/065* (2016.02); *A61B 2562/0219* (2013.01); *A61B 2562/0223* (2013.01); *A61B 2562/0261* (2013.01); *A61B 2562/164* (2013.01); *A61B 2562/182* (2013.01); *A61B 2562/187* (2013.01); *A61B 2562/22* (2013.01)
(58) Field of Classification Search
  CPC ........ A61B 2090/064; A61B 2090/065; A61B 2017/2905
  See application file for complete search history.

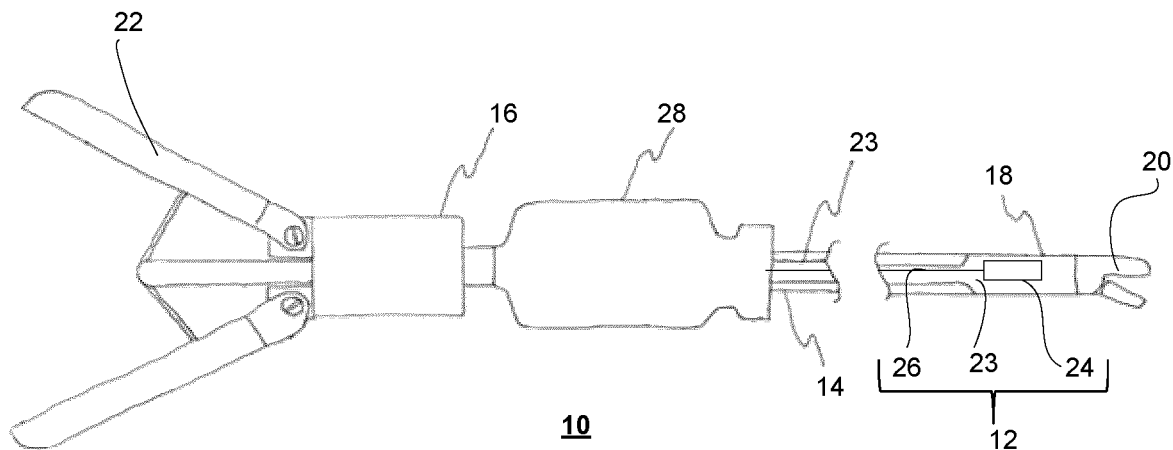
Figure 1
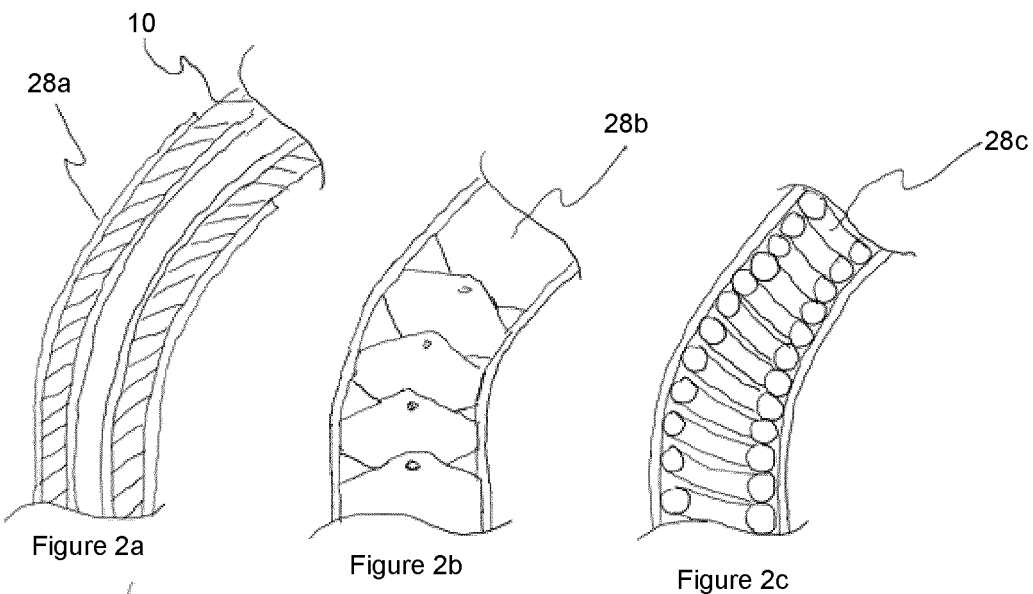
Figure 2a
Figure 2b
Figure 2c
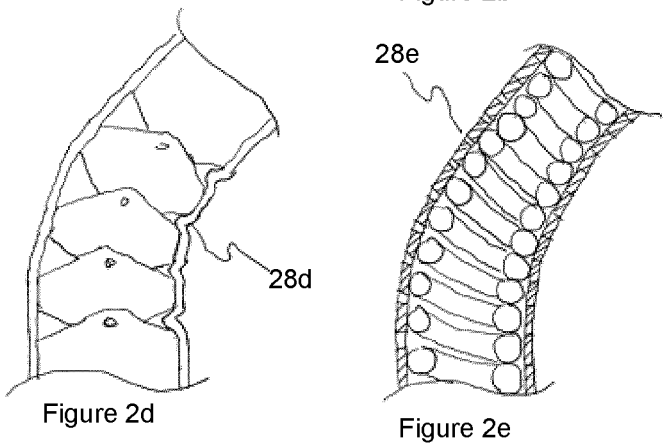
Figure 2d
Figure 2e

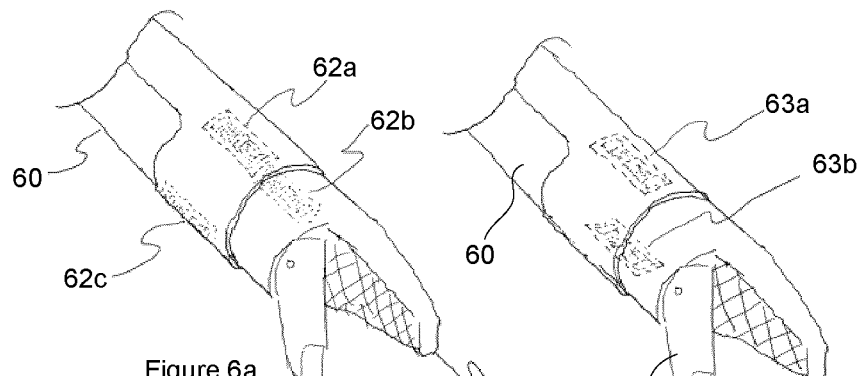
Figure 6a
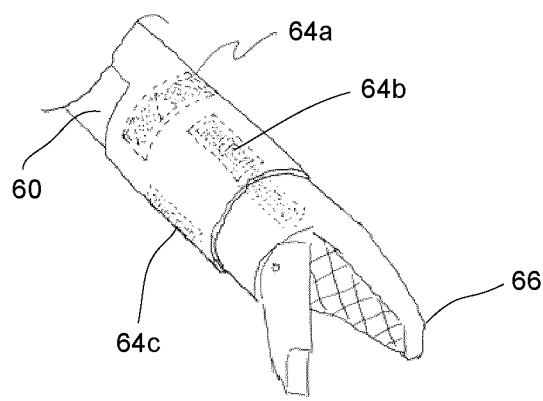
Figure 6b
Figure 6c
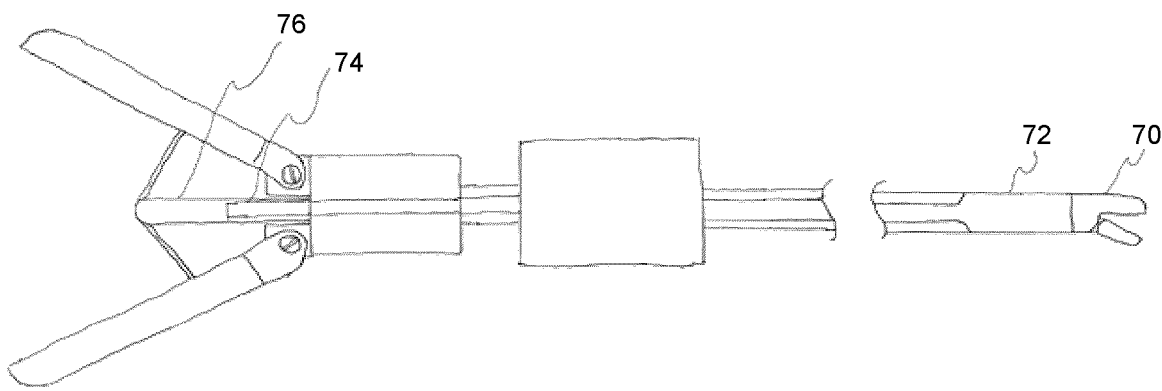
Figure 7

SENSOR FILM FOR ENDOSCOPIC INSTRUMENTS

FIELD OF THE INVENTION

The present invention relates to endoscopic surgery and more particularly to endoscopic instruments associated with one or more sensors.

BACKGROUND

Traditional open surgery uses surgical tools and techniques that put the surgeon in direct contact with tissue at the surgical site. Accordingly, surgeons are able to assess the amount of force they are applying to the often delicate tissue when operating with help of surgical tools. Generally, the application of excessive forces on the tissue may lead to damage, such as bruising, tearing, or worse. While traditional open surgery gives surgeons some control of the force on the tools, this type of surgery requires a large amount of dissection to reach internal surgical sites. In order to significantly reduce the amount of dissection required to access the surgical site, traditional surgery is being replaced with endoscopic surgery.

Endoscopic surgery is a method of surgery in which elongated tools are inserted through small incisions made on the body. These endoscopic tools, or instruments, consist of a proximal handle, an elongated member extending from the handle, and a distal end effector. End effectors may be, but are not limited to, graspers, snares, scissors, needles, or retractors. Endoscopic instruments are inserted into the body through trocars which provide a conduit for the endoscopic instruments. Trocars consist of a sharp, removable distal tip, a hollow medical tube, and a proximal bulb. Generally, the trocar is inserted into the body through a small incision dimensioned to fit the sharp, removable tip, and the trocar is advanced into the body until the tip reaches the surgical site. Trocars are manufactured in standard sizes for trocar and endoscopic instrument interoperability. In addition to creating the channels into the body and protecting the surrounding tissue from damage from tool friction, the trocars can also act as a port for injecting a gas, such as nitrogen, oxygen, or air into the cavity to expand the cavity and create a larger working area for the endoscopic instruments. The gap between the endoscopic instrument and trocar is minimized to prevent the gas from escaping.

While endoscopic surgery significantly reduces the amount of dissection required to reach internal surgical sites, it also introduces a host of problems for the surgeon to contend with. Trocars create a fulcrum effect which changes the mechanical advantage of an endoscopic instrument as it is translated in or out of the trocar. The instruments are often at much higher or lower mechanical advantage due to length of the instruments. Finally, trocars create friction that varies with lubrication and loading perpendicular to the medical tube. All of these mechanics make it significantly more difficult for surgeons to accurately assess the amount of force they apply to the tissue. Given that most tissue is relatively delicate, excessive application of force can bruise, tear, and kill tissue leading to surgical complications, poorer surgical outcomes, and/or patient discomfort. Additionally, tying suture knots requires a precise application of force, as tying the knot too tightly can cause the tissue being joined to die, while tying too lightly can lead to leakage or poor healing.

Various approaches have been proposed in an attempt to measure forces applied to the tissue when using endoscopic instruments. For example, in one approach distal sensors are coupled to the exterior of the instrument using wiring inserted in grooves that are machined into the shaft of the instrument. However, this method requires the instrument to be modified to accommodate the sensors and create the grooves in the shaft of the instrument.

In yet another approach, a sheath with sensors and wiring embedded therein is placed over the instrument. However, these sheaths are too thick to fit between an existing endoscopic instrument and its intended size of trocar, therefore either the next larger size of trocar must be used, or the trocar or the instrument must be redesigned to accommodate the increased bulk. Additionally, the sheath is an extra item that must be sterilized and, since the sheath is not in perfect contact with the shaft of the instrument, the sensor readings may not be recorded, and therefore some time periods may have missing sensor readings. This inconsistency in the sensor readings renders this approach unreliable and unsuitable.

In yet another approach, distal sensors are coupled with wiring on the interior of the instrument. However, this approach requires the sensors to be built into the instrument during manufacturing or requires the instrument to be designed to be disassembled.

It is an object of the present invention to mitigate or obviate at least one of the above-mentioned disadvantages.

SUMMARY OF THE INVENTION

In one of its aspects, there is provided an endoscopic instrument for use with a trocar, said endoscopic instrument comprising:
   an elongate shaft body having a proximal end and a distal end;
   an end effector assembly at said distal end operable by manipulation of actuator mechanism at said proximal end;
   a substrate core having a first surface and a second surface; and wherein said substrate is conformally attached to said elongated shaft body
   at least one sensing element on said elongate shaft body, said at least one sensing element located adjacent to said distal end;
   an electronics module for receiving sensed signals from said at least one sensing element, said electronics module located adjacent to said proximal end;
   a first conductive layer residing on said first surface, said first conductive layer having a first solder mask coated thereon; and
   a second conductive layer residing on said second surface, second conductive layer having a second solder mask coated thereon, and wherein said second conductive layer coupled to said at least one sensing element relays said sensed signals from said at least one sensing element to said electronics module and said a first conductive layer is grounded.

In another of its aspects, there is provided an endoscopic instrument for use with a trocar, said endoscopic instrument comprising:
   an elongate shaft body having a proximal end and a distal end;
   an end effector assembly at said distal end operable by manipulation of actuator mechanism at said proximal end;
   a substrate core having a first surface and a second surface; and wherein said substrate is conformally attached to said elongated shaft body;

at least one sensing element on said elongate shaft body, said at least one sensing element located adjacent to said distal end;

an electronics module for receiving sensed signals from said at least one sensing element, said electronics module located adjacent to said proximal end;

a first conductive layer residing on said first surface, said first conductive layer having a low friction, non-conductive layer thereon;

a second conductive layer residing on said second surface, second conductive layer having a solder mask coated thereon, and wherein said second conductive layer coupled to said at least one sensing element relays said sensed signals from said at least one sensing element to said electronics module and said a first conductive layer is grounded; and said low friction, non-conductive layer is adhered to first conductive layer via an adhesive to surround edges of said substrate core, second conductive layer and solder mask.

In another of its aspects, there is provided an endoscopic instrument for use with a trocar, said endoscopic instrument comprising:

an elongate shaft body having a proximal end and a distal end;

an end effector assembly at said distal end operable by manipulation of actuator mechanism at said proximal end;

at least one sensing element on said elongate shaft body, said at least one sensing element located adjacent to said distal end;

an electronics module for receiving sensed signals from said at least one sensing element, said electronics module located adjacent to said proximal end;

an upper substrate core;

a lower substrate core; and wherein said upper substrate core and said lower substrate core are conformally attached to said elongated shaft body;

an intermediate conductive layer between said upper substrate core and said lower substrate core;

a first conductive layer residing on said upper substrate core, and said first conductive layer having a first solder mask coated thereon;

a second conductive layer residing below said second conductive layer, and having a second solder mask coated thereon; and wherein said intermediate conductive layer relays said sensed signals, and said first conductive layer and second conductive layer are grounded.

In another of its aspects, there is provided an endoscopic instrument for use with a trocar, said endoscopic instrument comprising:

an elongate shaft body having a proximal end and a distal end;

an end effector assembly at said distal end operable by manipulation of actuator mechanism at said proximal end;

a substrate core having a first surface and a second surface; and wherein said substrate is conformally attached to said elongated shaft body;

at least one sensing element on said elongate shaft body, said at least one sensing element located adjacent to said distal end;

an electronics module for receiving sensed signals from said at least one sensing element, said electronics module located adjacent to said proximal end;

a sheet of grounded ferromagnetic metal residing on said first surface, said a sheet of grounded ferromagnetic metal; and a conductive layer residing on said second surface, second conductive layer having a solder mask coated thereon, and wherein said second conductive layer is coupled to said at least one sensing element to relay said sensed signals from said at least one sensing element to said electronics module.

In another of its aspects, there is provided an endoscopic instrument for use with a trocar, said endoscopic instrument comprising:

an elongate shaft body having a proximal end and a distal end;

an end effector assembly at said distal end operable by manipulation of actuator mechanism at said proximal end;

at least one sensing element on said elongate shaft body, said at least one sensing element located adjacent to said distal end;

an electronics module for receiving sensed signals from said at least one sensing element, said electronics module located adjacent to said proximal end;

an upper substrate core;

a lower substrate core; and wherein said upper substrate core and said lower substrate core are conformally attached to said elongated shaft body;

an intermediate conductive layer between said upper substrate core and said lower substrate core;

a sheet of grounded ferromagnetic metal residing on said upper substrate core, and said sheet of grounded ferromagnetic metal first conductive layer having a low friction, non-conductive layer;

a second conductive layer residing below said second conductive layer, and having a second solder mask coated thereon; and wherein said low friction, non-conductive layer is adhered to said sheet of grounded ferromagnetic metal via an adhesive and around edges of said upper substrate core, a lower substrate core, intermediate conductive layer, second conductive layer and second solder mask; and wherein said intermediate conductive layer relays said sensed signals, and said sheet of grounded ferromagnetic metal and second conductive layer are grounded.

In another of its aspects, there is provided a method for sensing at least one property associated with an end effector of an endoscopic instrument during a surgical procedure, wherein said endoscopic instrument is used via a trocar, said endoscopic instrument comprising an elongate shaft body having a proximal end and a distal end, and an end effector assembly at said distal end operable by manipulation of actuator mechanism at said proximal end; said method comprising the steps of:

securing a sensor film conformally on said elongate shaft body, said sensor film comprising:

a substrate core having a first surface and a second surface; and wherein substrate core is conformally attached to said elongated shaft body;

at least one sensing element located adjacent to said distal end;

a first conductive layer residing on said first surface, said first conductive layer having first solder mask coated thereon, and wherein said first conductive layer is grounded;

a second conductive layer residing on said second surface, second conductive layer having a second solder mask coated thereon, and coupled to said at least one sensing element;

causing said at least one sensing element to measure at least one property and output a sensed signal and to convey said sensed signal via said second conductive layer to an electronics module;

at said an electronics module, receiving said sensed signal and processing said sensed signal to determine said property.

In another of its aspects, there is provided a sensor film comprising:

a substrate core having a first surface and a second surface;

at least one sensing element for sensing at least one property;

a first conductive layer residing on said first surface, said first conductive layer having first solder mask coated thereon, and wherein said first conductive layer is grounded; and a second conductive layer residing on said second surface, second conductive layer having a second solder mask coated thereon, and coupled to said at least one sensing element.

Advantageously, the present invention provides a sensor film that can be readily associated with a standard surgical instrument, such as an endoscopic instrument, in order to add sensing capability or functionality to the surgical instrument. The sensor film comprises a thin conformal substrate, which allows an existing endoscopic instrument to communicate with sensors at the distal tip of the instrument without modification. The sensor film is dimensioned such that the instrument with the sensor film can be used with the existing trocar intended for the instrument, and without requiring that the sensors and wiring be built into the instrument during manufacture or require the ability to disassemble the tool.

The signals detected by the sensor film are processed and interpreted, and relayed to the surgeon to provide real-time feedback, and alerts based on predetermined thresholds. More specifically, the standard surgical instrument is retrofitted with the sensor film, thereby foregoing the acquisition costs and maintenance costs associated with specialized sensing surgical instruments. In addition, the sensor films are interchangeable, such that multiple sensors may be associated with any particular instrument, which adds versatility to any instrument. Accordingly, should a sensor film, or sensors, fail then only the sensor film will require replacement, and not the entire instrument, as is common with some of specialized prior art sensing surgical instruments.

BRIEF DESCRIPTION OF THE DRAWINGS

Several exemplary embodiments of the present invention will now be described, by way of example only, with reference to the appended drawings in which:

FIG. 1 shows an endoscopic instrument associated with a sensor film;

FIGS. 2a to 2e show various flexible proximal shaft configurations;

FIGS. 6a to 6c show various strain gauge configurations;

FIG. 7 shows positioning of additional sensing elements on the endoscopic instrument;

DETAILED DESCRIPTION OF EXEMPLARY EMBODIMENTS

Figure 3A:
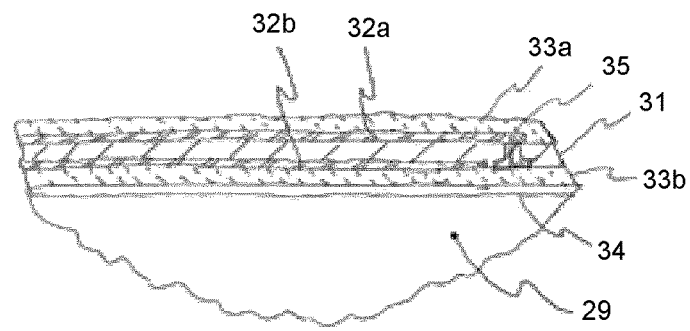
FIGS. 3a to 3e show various substrate laminations.

The detailed description of exemplary embodiments of the invention herein makes reference to the accompanying block diagrams and schematic diagrams, which show the exemplary embodiment by way of illustration. While these exemplary embodiments are described in sufficient detail to enable those skilled in the art to practice the invention, it should be understood that other embodiments may be realized and that logical and mechanical changes may be made without departing from the spirit and scope of the invention. Thus, the detailed description herein is presented for purposes of illustration only and not of limitation. For example, the steps recited in any of the method or process descriptions may be executed in any order and are not limited to the order presented.

Moreover, it should be appreciated that the particular implementations shown and described herein are illustrative of the invention and its best mode and are not intended to otherwise limit the scope of the present invention in any way. Connecting lines shown in the various figures contained herein are intended to represent exemplary functional relationships and/or physical couplings between the various elements. It should be noted that many alternative or additional functional relationships or physical connections may be present in a practical system.

FIG. 1 shows an exemplary surgical instrument 10, such as an endoscopic instrument for use in minimally invasive surgery, with exemplary sensor film 12. As can be seen, surgical instrument 10 comprises elongate shaft body 14 with proximal end 16 and distal end 18, and end effector assembly 20 at distal end 18 operable by manipulation of actuator mechanism 22 at proximal end 18. Accordingly, actuator mechanism 22 and end effector assembly 20 are interconnected via a push rod or wire (not shown) within elongate shaft body 14. Sensor film 12 comprises substrate 23 with one or more sensing elements 24 coupled to a communication medium 26 extending therefrom for relaying sensed signals to electronics module 28 at proximal end 16 for processing. Generally, sensor film 12 is placed onto elongate shaft body 14, and secured thereto by attachment means, such that sensing elements 24 are disposed adjacent to distal end 18 with end effector 20. Substrate 23 is relatively thin, and is laminated onto the elongate shaft body 14 without any protrusion or flap such that it does not catch on the trocar as the endoscopic instrument 10 translates in or out of the trocar. Additionally, the substrate 23 and sensing elements 18 are dimensioned to fit between the endoscopic instrument 10 and trocar. Communication medium 26 may include, but is not limited to, electrical traces, fiber optics, or any combination thereof. In one exemplary implementation, one or more layers of polyimide with gold, silver, or copper electrical traces is used as or part of the thin conformal substrate 23. Electronics module 28 comprises at least an analog front end for interpreting sensor signals. Additionally, the electronics module 28 may contain, but is not limited to, wired and/or wireless communication interface, power source, power circuitry, battery, battery charging circuit, sensors, logic circuits, microprocessors, or any combination thereof. Additional sensors may include, but are not limited to, accelerometers, gyroscopes, capacitive touch, temperature, pressure, humidity, wireless antenna, magnetic sensor, tilt sensor, or any combination thereof.

As shown in FIG. 2, thin substrate 23 may also be flexible or semi-flexible to match a flexible or semi-flexible endoscopic instrument 20. In the case of flexible or semi-flexible instruments, thin substrate 21 is preferably composed of materials 28a that exceed the elastic limit of the material or the effective elastic limit of the elongated shaft body 14 of endoscopic instrument 10. The effective elastic limit is used where the geometry or assembly of the elongated shaft body 14 allows it to exceed the elastic limit of its constituent materials such as, but not limited to, hinges 28b, springs 28c, as shown in FIGS. 2b and 2c, respectively, and spiral cut tubes (not shown). Substrate 23 may also have its effective elastic limit increased to match the endoscopic instrument by modification in geometry such as, but not limited to, folds 28d or cuts 28e in substrate 23, as shown in FIGS. 2d and 2e, respectively.

Figure 3B:
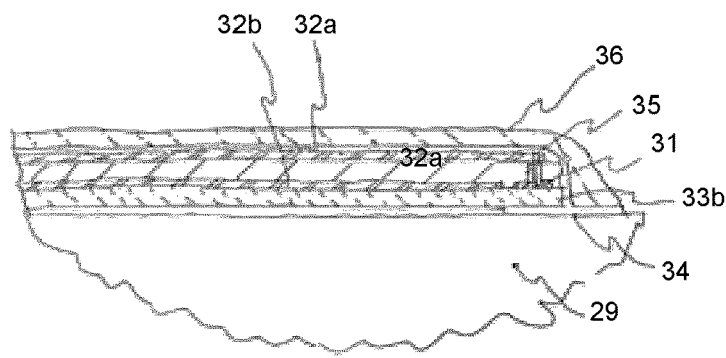
Figure 3C:
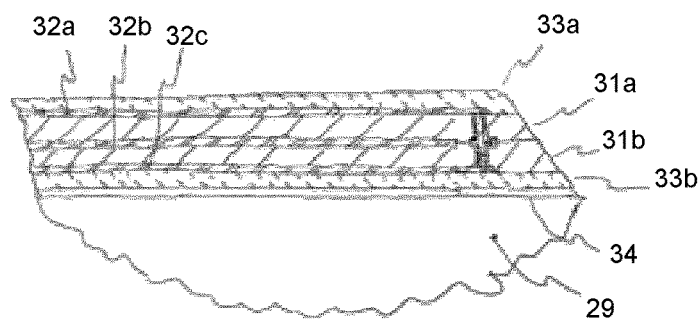

In another exemplary implementation, as shown in FIGS. 3a to 3c, substrate 31 includes built-in shielding to extraneous noise signals. Preferably the shielding comprises substrate material or lamination able to minimize the effects of radiative, capacitive, inductive, magnetic, or conductive interference to sensor film 12. The shielding may be implemented as the only noise filter, or in addition to shielding on the sensing elements 24, including circuitry associated therewith, and communication medium 26, or analog or digital filtering.

In one exemplary implementation, as shown in FIG. 3a, elongated shaft body 29 of endoscopic instrument 10 comprises longitudinal substrate core 31 with opposing surfaces carrying conductive material and solder mask coated thereon. Substrate core 31 with the masked conductive material is placed on elongated shaft body 29 and secured thereon by adhesive 30. In more detail, substrate core 31, such as polymide, or any similar material, is sandwiched between upper conductive layer 32a and lower conductive layer 32b. Upper conductive layer 32a acts as a grounded shield, while bottom conductive layer 32b relays sensor signals from sensing elements 24 to electronics module 28. Upper conductive layer 32a is insulated with a solder mask 33a, while bottom conductive layer 32b is insulated with a solder mask 33b. Preferably, solder mask 33a and solder mask 33b are medical grade. In this configuration the metal elongate shaft body 29 of endoscopic instrument 10 acts as an additional shield. Additionally, an edge stitching 35 or similar, such as, but not limited to, edge metallization or conductive coating, may be used to extend the shielded ground from upper conductive layer 32a around the edge of lower conductive layer 32b which carries the sensed signals, which enhances the shielding protection. The shielding protects the circuit from direct conducted noise and radio frequency noise and also provides some protection to capacitive coupling. Also, there is additional protection from inductive noise if elongate shaft body 29 of endoscopic instrument 10 is composed of a ferromagnetic material such as, but not limited to, martensitic or ferritic grades of stainless steel.

In another exemplary implementation, as shown in FIG. 3b, the upper-side of solder mask 33a is replaced with a low friction, non-conductive material, such as a polymer, fluorinated ethylene propylene (FEP), polyurethane, polytetrafluoroethylene (PTFE), or similar. The low friction, non-conductive material which is adhered to upper conductive layer 32a as a layer via adhesive 30, around the side of the other layers 31, 32b, 33b to the endoscopic instrument 10. The low friction, non-conductive material 36 reduces the sliding resistance of the endoscopic instrument 10 as endoscopic instrument 10 travels within the trocar. In addition, the low friction, non-conductive material 36 improves wear resistance of endoscopic instrument 10, creates a higher resistance to conducted noise, and improves the dielectric strength.

In another exemplary implementation, as shown in FIG. 3c, two layers of polyimide 31a and 31b and three layers of conductive material 32a, 32b, and 32c are included. Upper conductive layer 32b conveying the sensor signals is sandwiched between polyimide layers 31a, 31b, while outer layers of conductive material 32a, 32c are both grounded shields which reduce capacitive coupling. In another exemplary implementation, looking at FIG. 3d, extending from the previous implementation shown in FIG. 3c, polyimide 31 comprises conductive layer 32 on one side and a sheet of grounded ferromagnetic metal 37 on the other side, instead of top conductive layer 32a of FIG. 3c. Ferromagnetic metal 37 reduces inductive noise protection, and may include, but is not limited to, ferritic grades of stainless steel. If the metal of the elongate shaft body 29 of endoscopic instrument 10 is also ferromagnetic, or if another sheet is place underneath the signal layer 32 of conductive material, then the circuit is substantially protected from inductive noise.

Figure 3D:
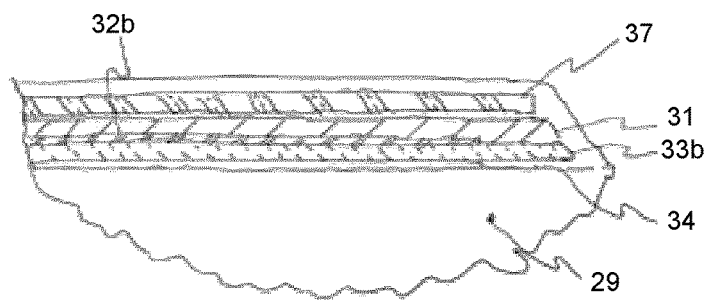
Figure 3E:
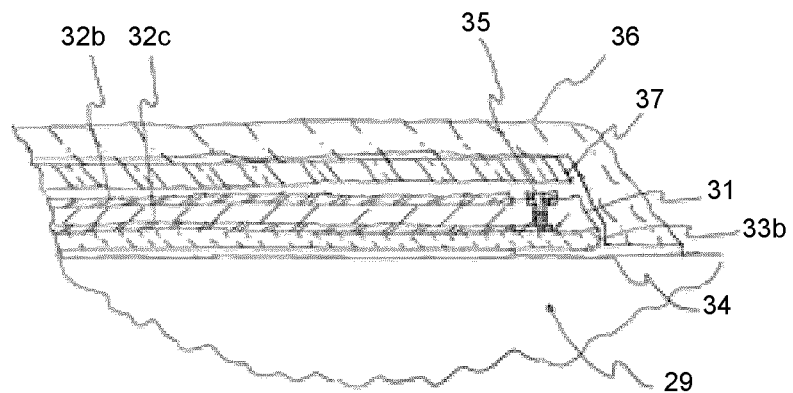

In yet another exemplary implementation, the features in the previous exemplary implementations of FIGS. 3b, 3c and 3d may be combined to aggregate the individual benefits. As an example shown in FIG. 3e, low friction, non-conductive material outer layer 36, such as PTFE, may be placed on top of ferromagnetic sheet 37 on top of double-sided polyimide 28 in which top conductive layer 32b relays the sensor signal and the bottom conductive layer 32c is a grounded shield. If the endoscopic instrument shaft 14 is ferromagnetic, then this provides substantial protection against conductive, capacitive, inductive, and radio frequency noise while improving wear resistance and sliding resistance.

Figure 4:
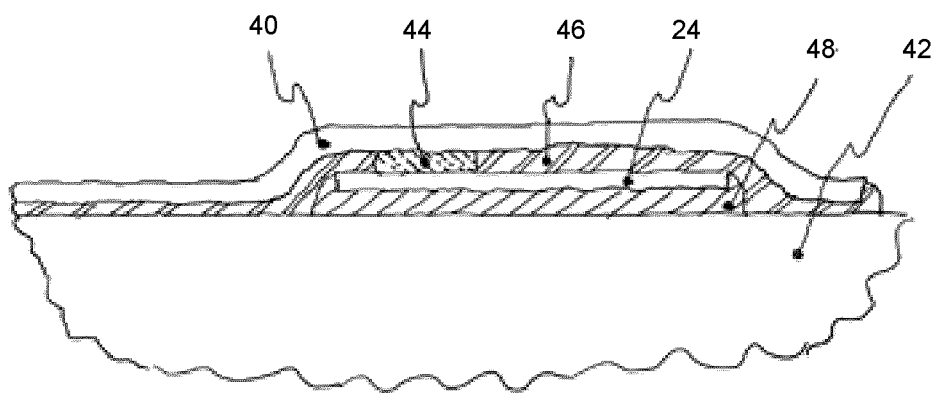
FIG. 4 shows a cross-section of a distal section of the endoscopic instrument with strain gauges.
Figures 5A, 5B:
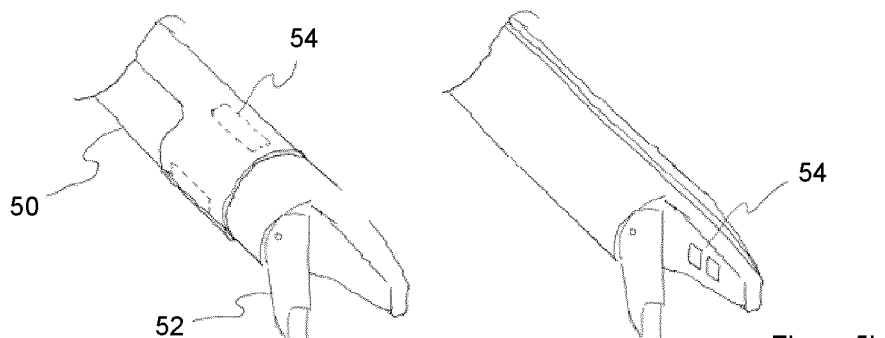
FIGS. 5a to 5e show different distal sensor types and configurations.
Figures 5C, 5D:
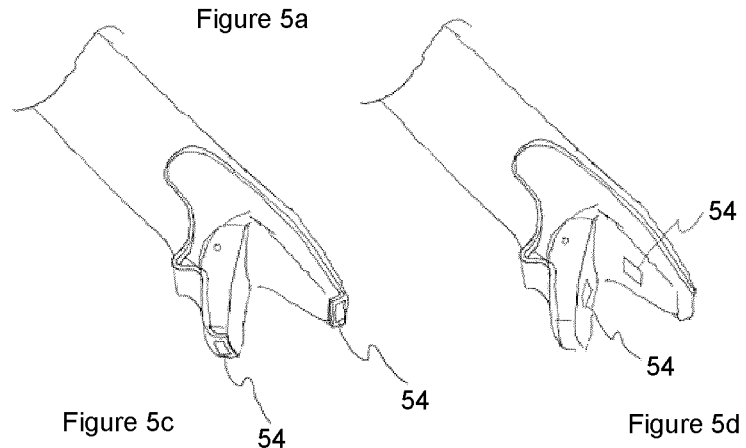
Figure 5E:
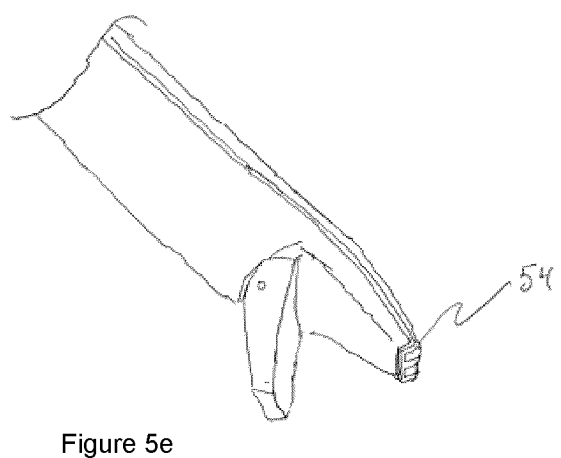

As shown in FIG. 4, sensor film 12 comprises substrate 40 with one or more sensing elements 24 secured to elongate shaft body 42 of endoscopic instrument 10. Generally, sensor film 12 is placed onto elongate shaft body 42, and secured thereto by attachment means, such that sensing elements 24 measure the desired property. In one exemplary implementation one or more sensing elements 24 are electrically-based, and include electrical coupling 44 made by, but is not limited to, welding, conductive epoxy, conductive adhesive, spring contacts, crimping, mechanical interlocking, brushes, low temperature solder, or any combination thereof. In addition to functional contact, sensing elements 24 may also be mechanically coupled via mechanical coupling means 46 to protect the functional contacts of sensing elements 24 and/or aid in the assembly thereof.

In one example, sensing elements 24 are implemented as metal or piezoelectric strain gauges in order to measure forces. As such, strain gauges 24 are configured to output a voltage signal based on a change in resistance when surgical instrument 10 to which they are attached to undergoes tension or compression. The one or more strain gauges 24 are mechanically coupled to the structural shaft 42 of the endoscopic instrument 10. The coupling of the strain gauges 24 is preferably accomplished with as thin an adhesive 48 as possible, with a hardness between that of the strain gauge 24 material and the shaft body 42 material. Adhesive 48 may be, but is not limited to, cyanoacrylate, epoxy, or acrylic. Additionally, the one or more strain gauges 24 may be welded to the structural shaft body 42 without or in addition to adhesive using, but not limited to, ultrasonic welding, solvent welding, melting, or some combination thereof. Also, the strain gauge 24 may comprises more than one strain gauge pattern in each gauge. For example, in one exemplary implementation, a second strain gauge pattern is placed perpendicular to the first strain gauge pattern to provide thermal compensation.

FIGS. 5*a* to 5*e* show different distal sensor types and configurations in which endoscopic instrument 10 comprises one or more sensing elements 54 on elongate shaft 50 and/or on end effector 52. Sensing elements 54 include, but are not limited to, strain gauges, radio frequency antennas, accelerometers, gyroscopes, magnetometers, piezoelectric, ultrasonic, capacitive, Braggs diffraction grating, thermometer, light sensor, or any array, part of a larger system, hybrid, application of or combination thereof such as, but not limited to, galvanic sensing, impedance spectroscopy, image sensing, photoplethysmogram (PPG), blood flow, pulse transit time (PTT), ballistocardiogram (BCG), electromyography (EMG), electrocardiography (ECG or EKG), electroencephalogram (EEG).

In another exemplary implementation, one or more strain gauges 62 are placed in a plurality of configurations, as shown in FIGS. 6*a* to 6*c*. For example, in FIG. 6*a*, strain gauges 62*a*, 62*b* and 62*c* are placed parallel to shaft 60 of instruments 10, and on opposite sides of shaft 60. This configuration allows the differentiation of one direction of bending and extension/compression which makes it useful for endoscopic instruments 10 that are intended to operate in a single bending direction such as, but not limited to, retractors and endoscopic instruments that are intended to operate in pure extension/compression such as, but not limited to, biopsy tools and neurosurgical tools.

In another exemplary implementation, two strain gauges 63*a*, 63*b* are placed parallel to shaft 60 of instrument 10 and equally spaced from each other, as shown in FIG. 6*b*. The equal spacing of the strain gauges 63*a*, 63*b* is preferred but other configurations are operable but will not provide overall optimal resolution of the two bending moments and compression and/or extension. This configuration allows the differentiation of both bending directions and extension/compression which makes it useful in surgical instruments 10 such as, but not limited to, graspers and needle drivers. In another exemplary implementation, as shown in FIG. 6*c*, strain gauge 64*a* with a pattern aligned roughly at 45 degrees to the endoscopic instrument shaft 60 is used to determine the torque on endoscopic instrument shaft 60 with additional strain gauge patterns 64*b*, 64*c* helping to determine bending moments, including compression and extension.

In situations where direct contact is required with the tissue, the one or more sensing elements 62*a*, 62*b*, 62*c*, 63*a*, 63*b*, 64*a*, 64*b*, and 64*c* may be, but are not limited to, being located beside, located through, or integrated into the end effector 66 or on the outside of the thin substrate 23 where the endoscopic instrument 10 may or may not be modified to accommodate the one or more sensing elements 62*a*, 62*b*, 62*c*, 63*a*, 63*b*, 64*a*, 64*b*, and 64*c*.

In another exemplary implementation, electrodes are placed on endoscopic instrument shaft 60, integrated in end effector 66, or both. These electrodes can be used for, but are not limited to, impedance spectroscopy, EMG, ECG, EEG, electrical stimulation, or any combination thereof. In one application, a combination of two or more of impedance spectroscopy, EMG, and electrical stimulation can be used to assess and monitor muscle viability.

As shown in FIG. 7, in addition to sensing elements 70 placed at the distal tip 72, one or more sensing elements 74 may be placed at any part of the mechanism which controls end effector 76 such as, but not limited to, pull rods or cables. Preferably, sensing elements 74 are placed at locations on endoscopic instrument 10 where no modification of the endoscopic instrument 10 is required.

In one exemplary implementation, one or more strain gauges at the distal portion of the endoscopic instrument 10 is augmented by an accelerometer, gyroscope, tilt sensor, or any combination in order to give both position and force information. In another exemplary implementation where an energy storage device is used, any energy storage device that can be manufactured to a small size and high energy density can be used and may include, but is not limited to, silver oxide, lithium, aluminum ion, zinc, thin film, supercapacitors, or any combination thereof.

In another exemplary implementation, one or more temperature sensors in the electronics module are used to compensate for thermal effects on the sensitive analog components. In another exemplary implementation, the electronics can be selected to be able to withstand steam sterilization known as autoclaving by selecting electrical components that are rated to exceed the typical temperature of autoclaving, which is 121° C., such as, but not limited to, automotive rated components and lithium poly-carbon monofluoride batteries and by protecting the components from direct exposure to steam by, but not limiting to, plating, coating, potting, enclosing in a sealed case, or any combination thereof. As an alternative to the previously mentioned implementation where steam sterilization known as autoclaving is used, the battery and/or electronics can be made removable so that the removable parts do not need to be selected to survive autoclaving.

In one exemplary implementation, sensor readings are relayed to the surgeon to provide visual, tactile, or auditory feedback. In an instance where the feedback is visual, the information can be displayed by, but not limited to, overlaying the information on an endoscope monitor, having a separate device to display the information, or having a software application to display the information on an existing device such as, but not limited to, a phone, tablet, laptop, computer, or display monitor.

Figure 8A:
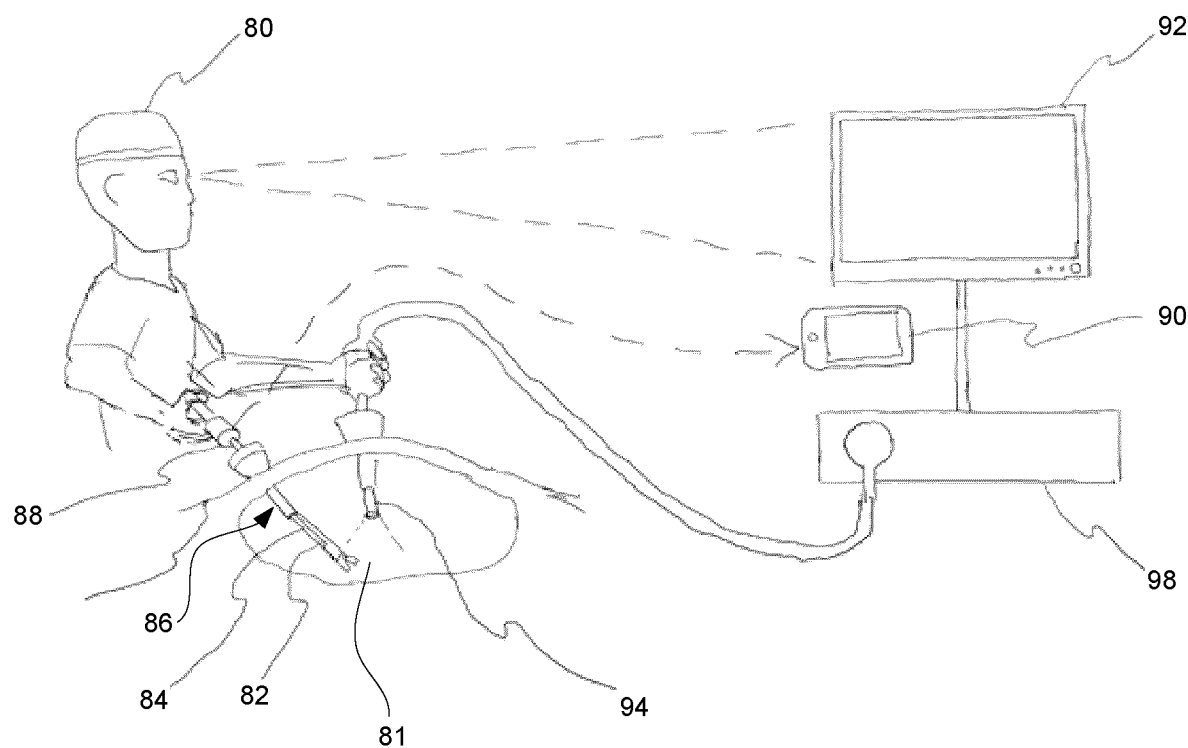
FIG. 8a shows a feedback system, in one exemplary implementation.

FIG. 8*a* shows a surgical feedback system which provides feedback to a user 80, such as a surgeon 80, or other medical professional, during a surgical operation on a body 81. Readings from sensors 82 associated with sensor film 84 conformally adhered to endoscopic instrument 86, are relayed to electronics module 88 via at least one of an electrical, infrared, optical, or radio connection. In one exemplary implementation, electronics module 88 uses radio communication and is powered by a power supply, such as a battery, such that there are no physical connections or line-of-sight issue constraining the movements of user 80 during surgery.

Electronics module 88 measures the sensor readings and transmits the data to feedback device 90 where user 80 receives the feedback and can modify their operation of the endoscopic instrument 86 accordingly. In one exemplary implementation, electronics module 88 communicates the feedback data, via radio transmission, to feedback device 90, such as a mobile device comprising, but not limited to, a smartphone, tablet, or laptop. The wireless communication to mobile device 90 allows medical trainees to quickly setup a feedback system and allows them to keep the gather data for later learning and analysis. Alternatively, electronics module 88 communicates the feedback data via a wired or wireless connection to a display monitor 92.

Figure 8B:
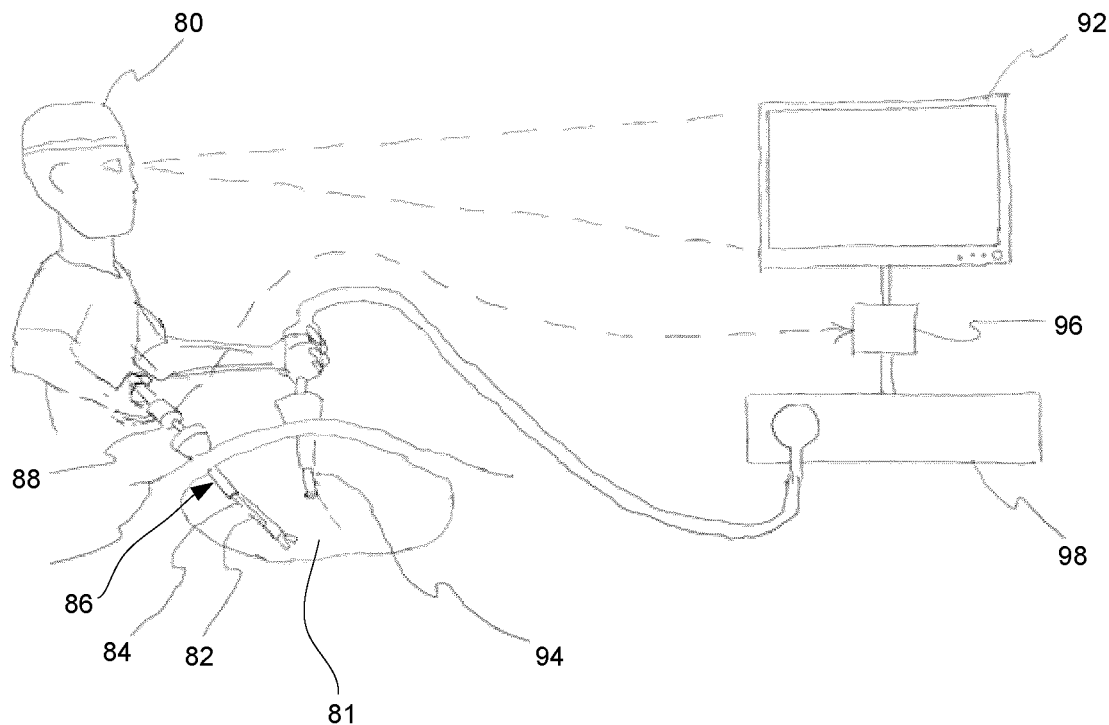
FIG. 8b shows a feedback system, in another exemplary implementation.

In another exemplary implementation, as shown in FIG. 8b, endoscope video imaging device 94 captures images pertaining to the surgical operation, and electronics module 88 communicates the sensed data, via radio transmission, to video overlay unit 96, such that the sensor information is overlayed over the video images from endoscope video unit 98, for display on monitor 92 in real time. This allows experienced surgeons 80 receive visual feedback from one or more sensors 82 on their endoscopic instrument 86 through the monitor 92 which they would be looking at view the video images from endoscope video unit 98.

In another exemplary implementation, the sensorized instruments may, but are not required to, operate with other sensorized instruments or sensors. The sensorized instruments or sensors may or may not have different sensors, sensor arrangements, number of sensors, or combination thereof. These sensorized instruments and/or sensors may, or may not, coordinate. Coordination can include, but is not limited to, sharing sensor data, synchronizing time, synchronizing events, requesting device operation changes, requesting data, requesting sensor readings be taken, or any combination thereof. These sensorized devices or sensors can be networked in any way or configuration. Networking can include, but is not limited to, planning instrument operation to not interfere with one another such that coordination between the devices is minimized, coordinating between sensorized instruments or sensors, coordinating with a central hub, or any combination thereof. Accordingly, two endoscopic needle drivers are used with the sensor-film communicates with strain gauges at the tips of the instruments. This configuration allows a complete assessment of the magnitude of the forces experienced in suture tying. These endoscopic needle drivers may, but are required to, have accelerometers and/or gyroscopes in their electronics modules in order to additionally capture the relative motion of suture tying.

In another exemplary implementation, one endoscopic instrument with a sensor-film communicates with an optical system at the tip of the instrument such as, but not limited to, PPG and an endoscope are used. The endoscope and sensorized instrument coordinate by momentarily turning the light of the endoscope off so that the optical system can perform its reading in darkness. This momentary turning off of endoscopic light can be done quickly enough such that the human eye does not notice and this can be done consistently to provide effectively simultaneous continuous reading in darkness and illumination for endoscopic viewing.

In another exemplary implementation, an endoscopic instrument with a sensor-film communicates with an electrically-based sensor and another endoscopic instrument utilizing electrical or radio-frequency energy such as, but not limited to, electrocautery, radio frequency ablation, or electrical stimulation are coordinated such that the electrical sensor is not reading and/or the electronics module is not connected while the electrical or radio-frequency energy tool is in operation. This coordination helps to ensure accurate sensor reading and protects the electronics module from damage.

In another exemplary implementation, PPG or BCG is used as the sensor and is integrated with the end effector. Most importantly, this allows the surgeon to assess local blood oxygenation during surgery in addition to other metrics. This system can, but does not have to, be combined with another PPG, BCG, or ECG equipped endoscopic instrument or external PPG, BCG, ECG, or other heart monitor to be used as part of PTT in order to assess blood pressure during surgery and/or in real time.

In another exemplary implementation, up to four strain gauges are placed at the distal portion of the endoscopic instrument at different points and direction such that they can capture all forces and torques experienced by the tip of the instrument which consists of two bending moments, torque, and compression or extension. The mechanical coupling to the endoscopic instrument is accomplished by epoxy. These strain gauges are then attached to a polyimide substrate with gold-plated copper electrical traces by conductive adhesive. The thin substrate finally attaches to an electronics module which comprises an analog front end, temperature sensor, Bluetooth transceiver, and battery. This allows the surgeon to see all of the forces experienced at the tip of the endoscopic instrument and record his motions in unison without any wires inhibiting the procedure. The readings from the temperature sensor are used to temperature compensate the readings from the analog front end for additional accuracy. This exemplary implementation makes no modification of the original endoscopic instrument and is completely wireless during surgery.

In another exemplary implementation in which the instrument undergoes steam sterilization known as autoclaving, the battery is a lithium poly-carbonmonofluoride battery, the components are all rated to above 121° C., the electronics module is a sealed case, and the electronics components are conformably coated, gold plated, and/or sealed. This allows the instrument to be sterilized without disassembling the device and prevents humidity-related inaccuracy and degradation of the analog front end but still allows access to the electronics for calibration and easy battery replacement.

In another exemplary implementation in which the endoscopic instrument has an end effector that requires one or more mechanical actuation rods or cables, additional strain gauges may be placed on the exposed proximal section of the pull rods or cables. The one or more additional strain gauges can be used to capture actuation forces as well as differentiate pull rod or cable forces from compression/extension caused by external forces.

While these exemplary implementations are described in sufficient detail to enable those skilled in the art to practice the invention, it should be understood that other exemplary implementations may be realized and that logical and mechanical changes may be made without departing from the spirit and scope of the invention. The preceding detailed description is presented for purposes of illustration only and not of limitation, and the scope of the invention is defined by the preceding description, and with respect to the attached claims.

The invention claimed is:

1. A medical instrument comprising:
   an elongate shaft body having a proximal end and a distal end;
   an end effector assembly at said distal end operable by manipulation of an actuator mechanism at said proximal end;
   at least one substrate core having a first surface and a second surface, and wherein said at least one substrate core is conformally attached to said elongate shaft body;
   at least one sensing element;
   an electronics module coupled to said at least one sensing element, said electronics module located adjacent to said proximal end, and wherein said at least one sensing element relays sensed signals to the said electronics module;

a first conductive layer residing on said first surface, said first conductive layer having a first solder mask coated thereon; and a second conductive layer residing on said second surface, second conductive layer having a second solder mask coated thereon, and wherein said second conductive layer coupled to said at least one sensing element relays said sensed signals from said at least one sensing element to said electronics module and said the first conductive layer is grounded, wherein said at least one substrate core comprises an upper portion and a lower portion separated by an intermediate conductive layer; and wherein said first conductive layer on said at least one substrate core is a sheet of grounded ferromagnetic metal.

2. The medical instrument of claim 1, wherein said first solder mask is a low friction, non-conductive layer, and wherein said low friction, non-conductive layer is adhered to first conductive layer via an adhesive to surround edges of said substrate core, second conductive layer and second solder mask.

3. The medical instrument of claim 1, wherein said at least one substrate core and said elongate shaft body is flexible.

4. The medical instrument of claim 1, wherein said at least one substrate core is composed of folds and cuts and materials that exceed the effective elastic limit of said elongate shaft body.

5. The medical instrument of claim 4, wherein said materials comprises at least one of hinges, springs, and spiral cut tubes.

6. The medical instrument of claim 1, wherein said at least one sensing element is placed on said elongate shaft body.

7. The medical instrument of claim 6, wherein said at least one sensing element comprises at least one of a radio frequency antenna, force sensor, accelerometer, gyroscope, magnetometers, piezoelectric sensor, ultrasonic sensor, capacitive sensor, Braggs diffraction grating, thermometer, or any array thereof, or a combination thereof.

8. The medical instrument of claim 1, wherein said at least one substrate core and said elongate shaft body is semi-flexible.

9. The medical instrument of claim 1, wherein said at least one sensing element is placed on said end effector assembly.

10. The medical instrument of claim 1, wherein said at least one sensing element is placed on said actuator mechanism.

11. The medical instrument of claim 1, wherein said at least one sensing element is placed on pull rods and/or cables associated with said actuator mechanism.

12. The medical instrument of claim 1, wherein said at least one sensing element is associated with at least one of galvanic sensing, impedance spectroscopy, image sensing, photoplethysmogram (PPG), blood flow, pulse transit time (PTT), ballistocardiogram (BCG), electromyography (EMG), electrocardiography (ECG or EKG), and an electroencephalogram (EEG).

13. The medical instrument of claim 1, wherein said medical instrument jog is used with a trocar.

14. The medical instrument of claim 1, wherein said medical instrument is useable with a port in a body.

15. A medical instrument comprising:

an elongate shaft body having a proximal end and a distal end;

an end effector assembly at said distal end operable by manipulation of an actuator mechanism at said proximal end;

at least one substrate core having a first surface and a second surface, and wherein said at least one substrate core is conformally attached to said elongate shaft body;

at least one sensing element;

an electronics module coupled to said at least one sensing element, said electronics module located adjacent to said proximal end, and wherein said at least one sensing element relays sensed signals to the said electronics module;

a first conductive layer residing on said first surface, said first conductive layer having a first solder mask coated thereon; and a second conductive layer residing on said second surface, second conductive layer having a second solder mask coated thereon, and wherein said second conductive layer coupled to said at least one sensing element relays said sensed signals from said at least one sensing element to said electronics module and said the first conductive layer is grounded;

wherein said first conductive layer on said at least one substrate core is a sheet of grounded ferromagnetic metal.

16. The medical instrument of claim 15, wherein said at least one substrate core is composed of folds and cuts and materials that exceed the effective elastic limit of said elongate shaft body.

17. The medical instrument of claim 16, wherein said first solder mask is a low friction, non-conductive layer, and said low friction, non-conductive layer is adhered to said sheet of grounded ferromagnetic metal via an adhesive and around edges of said substrate core, intermediate conductive layer, second conductive layer and second solder mask.

18. The medical instrument of claim 17, wherein said intermediate conductive layer relays said sensed signals and said second conductive layer is a grounded shield.

* * * * *